(12) United States Patent
Leinsing

(10) Patent No.: US 8,177,768 B2
(45) Date of Patent: May 15, 2012

(54) VIAL ADAPTER HAVING A NEEDLE-FREE VALVE FOR USE WITH VIAL CLOSURES OF DIFFERENT SIZES

(75) Inventor: Karl R. Leinsing, Hampton, NH (US)

(73) Assignee: CareFusion 303, Inc., San Diego, CA (US)

( * ) Notice: Subject to any disclaimer, the term of this patent is extended or adjusted under 35 U.S.C. 154(b) by 1835 days.

(21) Appl. No.: 11/061,290

(22) Filed: Feb. 18, 2005

(65) Prior Publication Data

US 2005/0148994 A1 Jul. 7, 2005

Related U.S. Application Data

(62) Division of application No. 10/072,052, filed on Feb. 8, 2002, now Pat. No. 6,875,205.

(51) Int. Cl.
*A61M 5/32* (2006.01)
(52) U.S. Cl. .......................................... 604/411
(58) Field of Classification Search ........... 604/411–414
See application file for complete search history.

(56) References Cited

U.S. PATENT DOCUMENTS

| | | |
|---|---|---|
| 4,128,098 A | 12/1978 | Bloom et al. |
| 4,296,786 A | 10/1981 | Brignola |
| 4,759,756 A | 7/1988 | Forman et al. |
| 5,334,179 A | 8/1994 | Poli et al. |
| 5,526,853 A | 6/1996 | McPhee et al. |
| 5,641,010 A | 6/1997 | Maier |
| 5,676,346 A | 10/1997 | Leinsing |
| 5,839,715 A * | 11/1998 | Leinsing ..................... 604/256 |
| 5,846,233 A | 12/1998 | Lilley et al. |
| 5,879,345 A | 3/1999 | Aneas |
| 5,893,397 A | 4/1999 | Peterson et al. |
| 6,019,750 A | 2/2000 | Fowles et al. |
| 6,063,068 A * | 5/2000 | Fowles et al. ............. 604/414 |
| 6,142,446 A | 11/2000 | Leinsing |
| 2003/9153895 | 8/2003 | Leinsing |

FOREIGN PATENT DOCUMENTS

EP 1 034 772 A1 8/2000

* cited by examiner

*Primary Examiner* — Melanie Hand
(74) *Attorney, Agent, or Firm* — McDermott Will & Emery LLP

(57) ABSTRACT

A vial adapter having a needle-free valve, a sharpened cannula used to perforate a vial's rubber stopper, and a circular array of claws of different lengths to engage vial closures of different diameters. The array of claws includes a first set of claws each having a first length extending inwardly from the periphery of the housing of the adapter and a second set of claws alternating with the first set of claws and each having a longer length. The second set of claws are mounted so that they deflect and plastically deform out of the way in the case where the adapter is engaged with a vial that exceeds a predetermined size. The housing includes a shroud that is at least as long as the sharpened cannula to protect medical personnel who use the adapter from inadvertent punctures. The needle-free valve includes a resiliently deformable piston element with a naturally open bore. The interior of the piston provides a fluid flow path through the adapter. In one embodiment, the first set of claws of the adapter may be used with a vial closure of at approximately 20 mm in diameter and the second set of claws may be used with a vial closure of approximately 13 to 17 mm in diameter.

28 Claims, 5 Drawing Sheets

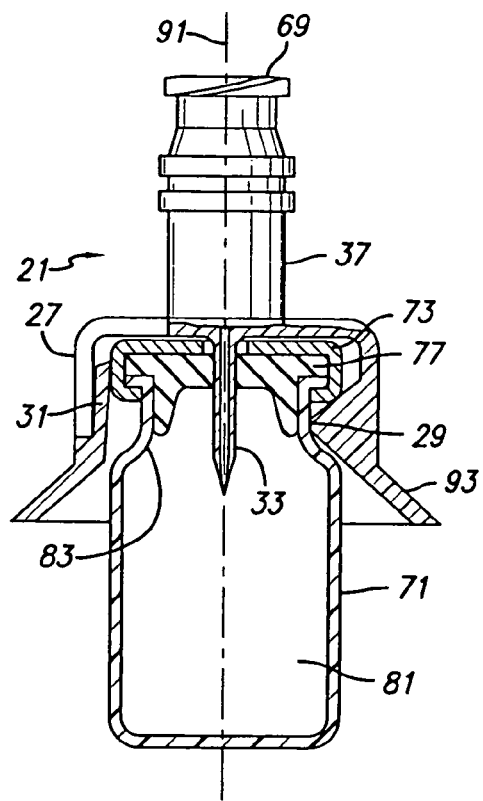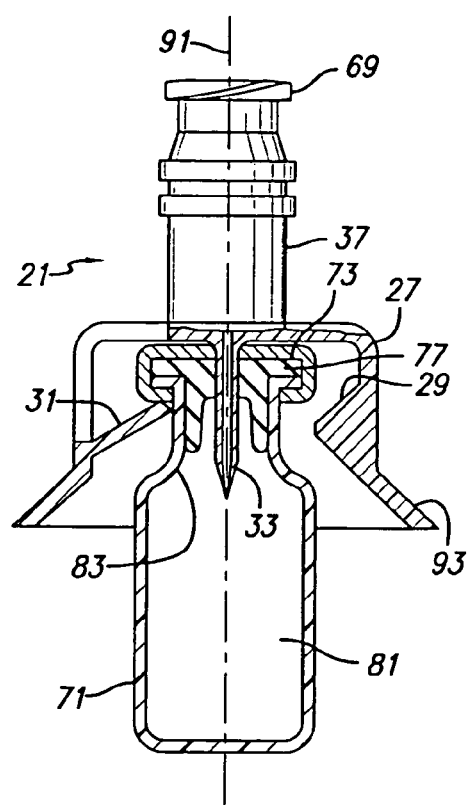
FIG. 5    FIG. 6
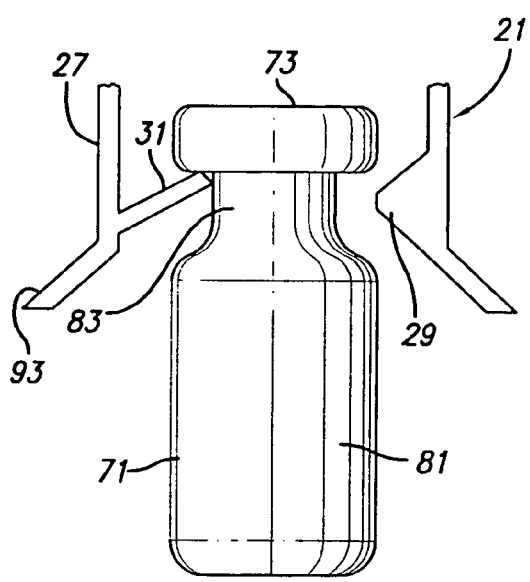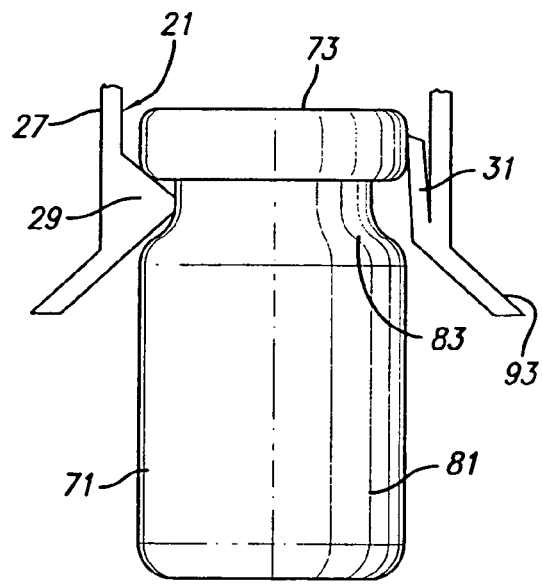
FIG. 7    FIG. 8

VIAL ADAPTER HAVING A NEEDLE-FREE VALVE FOR USE WITH VIAL CLOSURES OF DIFFERENT SIZES

This is a division of application Ser. No. 10/072,052, filed on Feb. 8, 2002 and now issued as U.S. Pat. No. 6,875,205, which is incorporated herein in its entirety.

BACKGROUND

The invention relates generally to connectors of the type used in the handling and administration of parenteral fluids, and more particularly, to a vial adapter having a sharp cannula for piercing a vial closure, a shroud protecting an operator from inadvertent puncture by the sharp cannula, and a valved connector opposite the sharp cannula for connection to another device for fluid flow.

Access ports for injecting fluid into or removing fluid from a system, such as a drug vial, are well known and widely used. Conventional injection sites in drug vials generally involve a pierceable rubber stopper formed of an elastomeric material such as butyl rubber or the like, placed in the opening of the vial. A closure, typically formed of metal, is crimped over the rubber stopper and the flange of the vial to positively hold the stopper in place in the opening of the vial. The closure has an outer size, known as a "finish size." The closure also has an opening, or access port, through which the stopper and the vial opening may be accessed. A sharp cannula is inserted into the access port piercing the rubber stopper to position the distal, open end of the cannula past the rubber stopper to make fluid connection with the interior of the vial.

Adapters have been found useful in that they can adapt the sharpened cannula that is placed into fluid communication with the vial to the connection device of another fluid container or fluid conduction device. For example, the adapter may include a female Luer fitting opposite the sharpened cannula to receive the nozzle of a syringe. The "adapter" therefore adapts the vial to the syringe, or adapts the sharpened cannula to the Luer-shaped nozzle of the syringe.

It has also been found useful to provide a means to attach or anchor the adapter to the vial to hold it in place while fluid communication between the vial and another device proceeds so that inadvertent disengagement of the adapter from the vial does not occur. For example, the adapter may have two arms that engage the neck or flange of the vial and hold the adapter in place on the vial. Other means include a shroud that fits around the outside of the vial closure and snaps onto the vial closure under the crimped retaining cap thereby grasping the vial neck flange and the underside of the closure.

It has also been found useful to have a valve placed in the adapter. The valved adapter permits engagement of the sharpened cannula with the contents of the vial without leakage of fluid from the vial through the adapter. Then when the second fluid device has been prepared, it can be connected to the adapter thereby activating the valve that then permits fluid flow between the vial and second device. One approach used today is to have two parts to result in a valved vial adapter. The vial adapter includes a sharpened cannula to pierce the stopper of a vial, and the other end of the adapter includes a female Luer connector. At the female Luer connector, a valve device having a male connector at one end is attached. While the vial adapter is then "valved," two parts were necessary to do so. It would be desirable to have a single part that not only adapts the vial to a blunt cannula, but one that also interposes a valve in between. Manufacturers of such medical devices strive for effective and reliable devices yet desire to keep costs as low as possible.

However, some of the existing adapters available today suffer from various shortcomings. For example, most adapters are designed to function only on a single vial closure finish size. These adapters do not securely attach to vial closures with diameters smaller or larger than vial closure finish sizes they are primarily molded to fit. They are therefore not usable on vials of other sizes. In addition, some vial adapters do not adequately protect an operator from inadvertent puncture of the operator's skin by the sharpened cannula of the adapter. The shroud or vial engagement device does not extend completely over the sharpened cannula, thus exposing operators to possible puncture.

Accompanying this limitation of functioning with only a single size of vial, a further consideration is the expense to hospitals or other medical facilities caused by having to stock numerous types and sizes of adapters. Vials of many flange sizes and closure sizes are available and are frequently found in medical care facilities. Typically a hospital must stock a variety of adapters to be assured of having the correct adapter available that will properly interconnect with the multiple vial closures that exist. If a hospital must maintain a stock of adapters for each possible size of closure, a logistical problem as well as increased expense can result. Two common sizes of vial closures are 13 mm vial closures and 20 mm vial closures. Reducing the number of adapters that must be stocked in a hospital can significantly lessen the problems with stocking the correct sizes and can reduce expenses.

It has also been a trend in recent years to provide needle-free valve devices in an effort to lower the risk of inadvertent punctures of health care personnel by sharpened devices. More recently, connectors or adapters for accommodating the injection and withdrawal of fluids without the use of sharp cannulas have been put to use in increasing numbers. This is due, at least in part, to concern regarding the possibility of the transmission of blood-borne diseases through accidental needle punctures of persons handling the sharp cannulas. Connectors having as few sharpened surfaces as possible are desirable because such hazard is thereby lessened.

Furthermore, it is desirable that needle-fee connectors be configured so that they can be easily cleaned by an antiseptic wipe, or otherwise sterilized, prior to making a connection. All exterior surfaces that may be involved in the transmission of fluid should be readily available for cleaning prior to the connection being made. Some prior connectors have a small rift or fissure defined by a clearance between parts. Such a feature is difficult and inconvenient to clean in attempting to sterilize a connector. Alternatively, connectors requiring a cap to maintain a sterile connection port prior to use are undesirable because the extra steps involved in removing and replacing a cap are inconvenient, while the manufacture of the cap adds expense.

Thus it would be desirable to provide a needle-free connector as part of the valve that is included in the adapter discussed above. This approach would increase safety for medical personnel who handle the adapter. Although certain vial adapters exist that can accommodate multiple sizes of vial closure finishes, a practical way to accommodate the large vial finish sizes is needed. Where a vial adapter is used to connect to both large and small vial finish sizes, the arms used for the small finish sizes must move out of the way when a large finish size must be accommodated. Arms that merely bend out of the way in such an application of the adapter can still exert relatively large pressure on the vial and tend to expel the vial from the adapter. Thus the small arms of such adapters work to retain the adapter to the vial while the longer arms work to separate the adapter from the vial. As is obvious, such an arrangement is undesirable. It is also undesirable to provide large arms that simply break away when encountering large finish sizes as then there would be small loose plastic parts that are not controlled. On the other hand, attempting to design break-away arms can increase expense as the arms must be designed to withstand a certain amount of force with the small vial finish sizes yet break away with the large vial finish sizes.

Hence, those concerned with the development of medical adapters have recognized the need for a single adapter that is usable with vials of different sizes. There has also been recognized a need for a protection device to be located around the sharpened cannula of such an adapter to protect operators from inadvertent punctures of their skin. Further, a need has been recognized for an adapter that can interconnect a vial with another fluid flow device by means of a needle-free valve so that sharpened needles are not needed that may also cause inadvertent needle punctures of operators. Further, a need has been recognized for a valve that is integral to the vial adapter. The invention fulfills these needs and others.

SUMMARY OF THE INVENTION

Briefly and in general terms, the invention is directed to a vial adapter for interconnecting with sealed vial closures of different diameters. In one main aspect, a vial adapter in accordance with the invention comprises a housing having a first end with an inner periphery with a circular array of claws, and having a second end, the housing having a thickness at the inner periphery and a sharpened cannula extending from the first end of the housing for penetrating a seal of a vial closure to establish fluid communication between the vial and the first end, wherein the array of claws comprises a first set of claws extending radially inwardly from the inner periphery, each of which has a first length, and a second set of claws extending radially inwardly from the inner periphery, each of the second set of claws having a second length that is longer than the first length of the first set of claws, each of the second set of claws adapted such that when the vial adapter is placed over a closure exceeding a selected diameter, each of the second set of claws will deflect and plastically deform thereby permitting the second set of claws to accommodate the larger closure. The length of each of the first set of claws is selected to engage a larger diameter vial closure and the length of each of the second set of claws is selected to engage a smaller diameter vial closure.

In further aspects, the second set of claws are thinner than the housing at the inner periphery and plastic deformation of the second set of claws occurs at or near the location at which the second set of claws are joined to the inner periphery. Further, the thickness of the second set of claws is selected so that when plastically deformed, the second set of claws do not apply a substantial force to the closure which may tend to decouple the vial adapter from the vial closure and the vial. In yet another aspect, the second set of claws comprises a narrowed segment at which the plastic deformation takes place.

In other aspects, the length of each of the second set of claws is selected such that when the adapter engages a smaller diameter vial closure, each of the second set of claws deforms elastically to engage the smaller vial closure. Further, the second set of claws deflect elastically as a result of a force directed axially through the center line of the vial adapter so that the second set of claws will snap under a crimped retaining cap surrounding a rubber stopper placed in the opening of the vial. In more detail, the second set of claws are located at the inner periphery so that they are alternating with the first set of claws about the inner periphery.

In more detailed aspects, the adapter housing further comprises a shroud forming a part of the adapter housing at the first end, the shroud extending from the first end far enough to surround the sharpened portion of the sharpened cannula to protect an operator of the vial adapter from inadvertent puncture by the sharpened cannula. The cannula comprises a protruding rib located so that when the cannula is engaged with the rubber stopper of a vial closure, the protruding rib resists rotation of the cannula once the sharpened cannula with the protruding rib have punctured the rubber stopper of the closure. The protruding rib is elongated and oriented parallel to a longitudinal axis of the central cannula. In another aspect, the cannula comprises a plurality of protruding ribs elongated and oriented parallel to a longitudinal axis of the central cannula.

In another detailed alternate aspect, each of the first set of claws has a terminal end and each of the second set of claws has terminal end and the terminal ends of the first set of claws and the terminal ends of the second set of claws are located in a common plane.

In yet further detailed aspects, a resealable needle-free valve is located in the second end of the adapter housing, wherein the needle-free valve opens to permit fluid flow upon insertion of a blunt cannula and closes to prevent fluid flow upon removal of such blunt cannula. The resealable needle-free valve comprises a valve housing within which is disposed a deformable piston element that provides a fluid flow path through its interior, the piston element having a naturally open bore wherein the bore is closed to prevent fluid flow when the needle-free valve is not accessed and wherein the bore opens to its naturally open shape to permit fluid flow when the valve is accessed. Yet further, the valve housing comprises a connection port, an exit orifice, a first section of a first cross-sectional size disposed adjacent the connection port, and a second section of a second cross-sectional size that is larger than the first section and the piston element comprises a deformable piston head in which the bore is formed, the piston head being movable from the first section of the housing as the needle-free valve is accessed and movable to the second section of the housing when the needle-free valve is not accessed, the first section having a size that deforms the piston head so as to occlude the bore, the second section having a size that allows the piston head to assume its natural shape in which the bore is open to provide a fluid flow path between the connection port and the exit orifice. In yet more aspects, the housing of the resealable needle-free valve comprises a connection port and an exit orifice and when the needle-free valve is accessed, the interior of the deformable piston element provides the fluid flow path through the needle-free valve between the connection port and the exit orifice.

Other features and advantages of the present invention will become apparent from the following detailed description of preferred embodiments which, taken in conjunction with the accompanying drawings, illustrate by way of example the principles of the invention.

BRIEF DESCRIPTION OF THE DRAWINGS

FIG. 5 is a partially broken away side view of the vial adapter attached to the vial having a 20 mm closure of FIG. 4, with the sharpened cannula penetrating the vial's stopper so that fluid communication with the vial is established;

FIG. 6 is a partially broken away side view of the vial adapter fully attached to a vial having a 13 mm closure, with the second set of hinged claws with the hinge structure engaging the 13 mm closure and the sharpened cannula penetrating the vial's stopper;

FIG. 7 is a non-cross sectional view of FIG. 6 showing the longer claw from the second set engaging the neck of the vial and the smaller vial closure while a claw from the first set of shorter claws is disengaged;

FIG. 8 is a non-cross sectional view of FIG. 5 showing a longer claw from the second set plastically deformed at the narrowed hinge and a claw from the first set engaging the neck of the vial and the larger vial closure;

In FIG. 9, each long claw is positioned between two short claws;

DETAILED DESCRIPTION OF PREFERRED EMBODIMENTS

Figure 1:
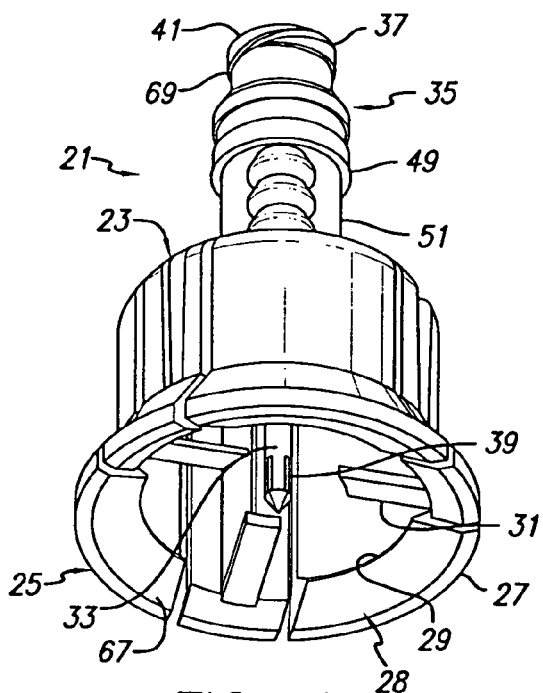
FIG. 1 is a perspective view of a vial adapter in accordance with principles of the present invention looking at the adapter from the sharpened cannula angle, the adapter having a Luer adapter with a needle-free site at one end, a shroud surrounding the sharpened cannula at the opposite end and a circular array of claws disposed at the inner periphery of the shroud and oriented radially inwardly toward the sharpened cannula for attaching to a vial closure which the sharpened cannula would perforate.

As shown in the drawings for purposes of illustration wherein like reference numerals designate corresponding or like elements among the several views, there is shown in the bottom perspective view of FIG. 1 a vial adapter 21 having a housing 23 with a first end 25 that includes a shroud 27 with a circular array of claws 28 surrounding a sharpened cannula 33, and a second end 35 that includes a resealable needle-free valve 37. Details of the resealable needle-free valve 37 are provided in U.S. Pat. No. 5,676,346 to Leinsing entitled NEEDLELESS CONNECTOR VALVE, issued on Oct. 14, 1997 and incorporated herein by reference, although the valve is discussed generally below. In FIG. 1, the circular array of claws can be seen to include multiple short claws 29 and long claws 31 (only one of each is indicated by the respective numeral to preserve the clarity of the drawing). It should be noted that the sharpened cannula 33 includes openings 39 through which fluid may be communicated.

Figure 2:
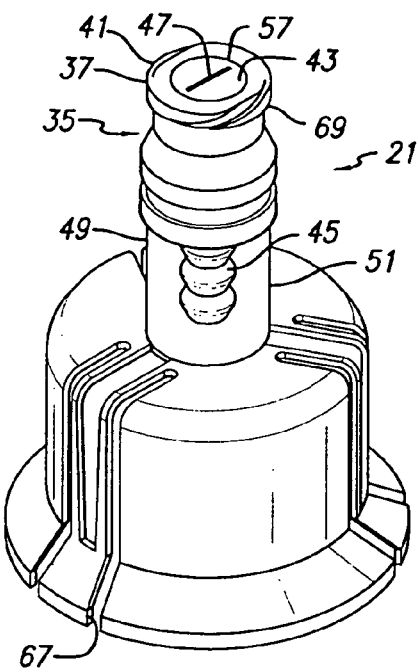
FIG. 2 is a top perspective view of the vial adapter in FIG. 1 looking at the adapter from the needle-free valve angle, and illustrating, in particular, the resealable needle-free site located at the female Luer adapter portion of the housing, and also showing the piston component of the needle-free valve portion of the adapter.

Referring now to the top perspective view of FIG. 2, the needle-free valve 37 can be more clearly seen. At the second end 35, the resealable needle-free valve 37 includes a female Luer connector 41. The Luer connector 41 is configured to receive all ANSI standard male Luer fittings, as well as other blunt cannulas or fluid conduit devices. The piston head 43 of a deformable piston element 45 can also be seen that has a naturally open bore 47, which in this case has been closed to prevent fluid flow through the adapter. The piston element 45 is, in this embodiment, located within a valve housing 49 that comprises a transparent tubular body portion 51 and the female Luer connector 41, which in this embodiment is opaque, mounted to the body portion 51.

Figure 3:
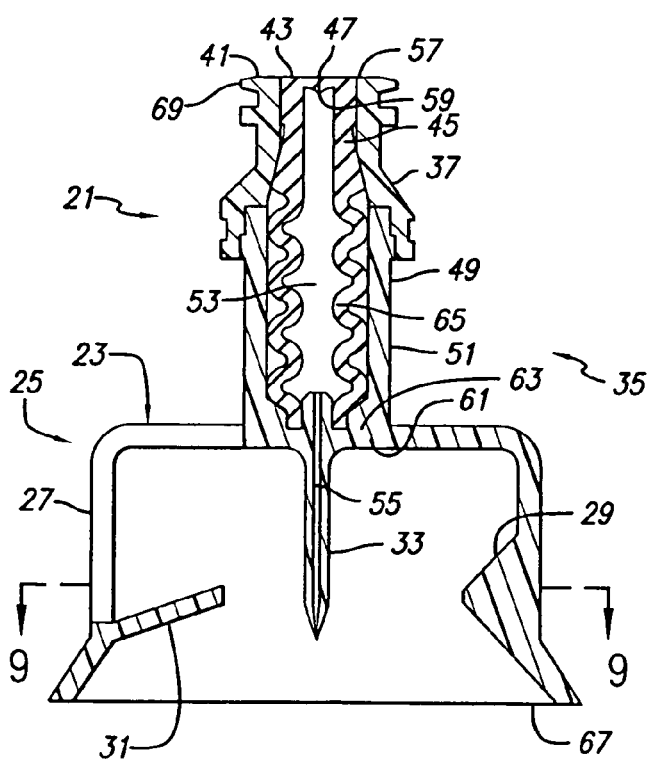
FIG. 3 is a cross-sectional view of the adapter of FIGS. 1 and 2 showing the adapter in its closed or inactivated state with the inactivated resealable needle-free site at one end, with a piston component in the interior of its housing, and a sharpened cannula at the opposite end surrounded by a slotted shroud with a partial view of a claw from the first set of claws and a hinged claw of the second set of claws respectively.

Turning now also to FIG. 3, a side, cross-sectional view is seen of the adapter of the perspective views of FIGS. 1 and 2. The piston element 45 has a hollow interior 53 that provides a fluid flow path completely through the needle-free valve 37 and into fluid communication with the lumen 55 of the sharpened cannula 33. The lumen 55 of the sharpened cannula 33 is in fluid communication with the openings 39 located at the sharpened tip of the cannula so that fluid communication can occur through the cannula 33. The view of FIG. 3 shows the vial adapter 21 unaccessed by a blunt cannula. However, the piston head 43 of the piston element 45 has a naturally open bore 47 that would permit fluid flow through the piston element when it is open. In the configuration of FIGS. 1, 2, and 3, the bore 47 has been forced closed by the difference between it and the female Luer opening 57 in the female Luer connector 41. More particularly, the piston head 43 is elliptical in shape and has a marquise-shaped bore 47. The size of the piston head 43 is selected so that when the piston head is constrained into the circular interior of the tapered opening 57 of the female Luer connector 41, the bore 47 is completely collapsed to tightly close off the fluid flow path 53. The adjacent lips 59 form a taper lip seal by abutting one another and applying further force to keep the bore closed when fluid pressure exists within the fluid flow path (interior) of the piston element when the valve is in its unaccessed state as shown in FIGS. 1 through 3. The lips comprise conical sections that extend from the bore's sides to function as a seal. The angle of the taper is selected so that internal pressure existing in the valve when the piston is in the closed state would force the lips toward one another thereby holding the bore closed.

The first end 25 of the housing 23 also includes a base 61 from whose center extends the sharpened cannula 33. The base also has a groove 63 in which is mounted the bellows portion 65 of the piston element. In this embodiment, the piston element 45 includes a total of four bellows, although more or fewer may be found to be appropriate in other embodiments. The bellows portion 65 provides a spring force to bias the piston head 43 into the female Luer opening 57.

The sharpened cannula 33 is disposed within the protective shroud 27 which is at least as long as the sharpened cannula 33 and surrounds the cannula to protect an operator of the adapter 21 from being punctured by the sharpened tip of the cannula 33. Furthermore, for simplicity, FIG. 3 shows only two claws, one from the first set of claws 29 and one from the second set of longer claws 31, formed at the inner periphery 67 of the shroud 27 surrounding the sharpened cannula 31. As is described in further detail below, and shown in other drawings, the claws are used as a means to retain and engage the mounted vial adapter 37 on a vial opening plugged with a rubber stopper and secured with an annular crimped retaining cap.

The female Luer connector 41 also includes external threads 69 to which a complementary thread cuff of a male Luer connector may be engaged to firmly hold the two connectors together.

Figure 4:
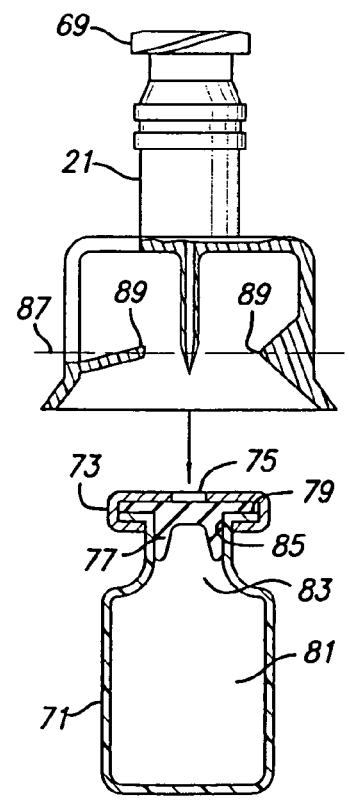
FIG. 4 is a partially broken away side view of the adapter with the shroud partially cut away and ready to be attached to a vial having a 20 mm closure.

FIG. 4 illustrates the application of the vial adapter 21 to a vial 71 having a closure 73. The sharpened cannula 33 will be moved through the opening 75 of the closure 73 and will be pressed through the rubber stopper 77 to establish fluid communication with the contents of the vial. The crimped retaining cap of the closure 73 covers the stopper 77, except for the opening 75, and is crimped around the bottom of the vial flange 79 as shown so that the stopper is held firmly in position in the vial. In some cases, the opening 75 of the closure includes a perforated, tear-away or bend-away cover (not shown). The operator pries the perforated cover up from the opening, which breaks the tabs between the perforations, and removes it entirely.

In more detail in regard to FIG. 4, the drug vial 71 includes a body 81 connected to a neck 83 which defines a passage into the body of the vial 71 and terminates in an outwardly extending flange 79 that defines an opening 85 into the vial 71. Thus, the opening 85 of the vial is surrounded by the outwardly extending flange 79 thereby creating a convenient ledge to which the closure 73 may be crimped to firmly hold the stopper 77 in the vial's opening 85.

Continuing to refer to FIG. 4, each claw of the first set of claws 29 and of the second set of claws 31 has a terminal end 89 and the terminal ends of the first set of claws and the terminal ends of the second set of claws are located in a common plane indicated by the dashed line having the numeral 87 in this embodiment. In other embodiments, the terminal ends of the claws are not located in a common plane. Additionally, the first set of claws and the second set of claws alternate along the inner periphery 67 of the shroud 27.

Referring now to FIGS. 1, 2, and 4, the shroud 27 in this embodiment is longer than the length of the sharpened cannula 33 and surrounds the sharpened cannula to protect an operator of the adapter 21 from being punctured by the sharpened tip of the cannula 33. Additionally, the shroud 27 is slotted to allow for selective bending outward to accept vial closures of larger sizes.

Referring particularly now to FIG. 5, the first step in using the vial adapter 21 is to place the end of the adapter including the sharpened cannula 33 surrounded by the shroud 27 next to the rubber stopper 77 of a vial 71. Next the vial adapter is manually pressed onto the closure 73 of the vial 71 with force directed axially through the centerline 91 of the sharpened cannula 33 sufficient to drive the sharpened cannula 33 into and through the rubber stopper. If the diameter of the vial closure is relatively large, for example 20 mm or greater, the second set of hinged claws 31 will deform plastically during the mounting motion of the adapter to the vial and bend up to a vertical or near-vertical position approximately parallel with the centerline 91 of the vial as shown in FIG. 5, and while the first set of shorter and rigid claws 29 will engage the larger vial closure.

The bottom of the shroud 27 in this embodiment includes a flared portion 93 that assists in guiding the shroud 27 over the closure 73 of a vial. In the embodiment shown, the flared portion extends beyond the sharpened tip of the cannula 33 to assist in guiding the shroud into the correct alignment with the vial closure before the sharpened tip 33 penetrates the closure.

In one embodiment, the first set of claws 29 having a shorter length are structured such that when the adapter is mounted on a vial with a vial closure of 20 mm±3 mm, the first set of claws will engage and retain the adapter 21 in position on the vial as shown in FIG. 5. During the engagement of the first set of claws 27 to the vial closure, the second set of longer hinged claws 31, used to engage vial closures of 13 mm±4 mm, plastically deform out of the way as shown in FIG. 5. Plastic deformation of the second set of claws 31 occurs when the claws are bent beyond a certain stress point. Further, the thickness of the second set of claws is selected so that when plastically deformed, the second set of claws do not apply a substantial force to the closure 73 that exceeds a selected diameter. Thus in the case shown in FIG. 5, the long claws 31 are plastically deformed as shown and do not exert relatively large pressure on the vial that may tend to expel the vial from the adapter. Instead, the deformed claws 31 exert little force against the retention of the vial closure and the vial within the adapter 21.

If the vial closure 73 is smaller as illustrated in FIG. 6 specifically in this embodiment, a closure that is 13 mm±4 mm in diameter, the first set of claws 29 will not engage the closure device but the second set of claws 31 will. As the vial adapter 21 is manually pressed onto the closure 73 of the vial 71 with force directed axially through the centerline 91 of the sharpened cannula 33, the second set of longer hinged claws 31 deform elastically during the mounting motion and snap under the crimped retaining cap 73 as shown in FIG. 6.

FIGS. 7 and 8 present schematic views of the operation of the claws with vial closures 73 of different sizes. FIG. 7 schematically presents the operation of the second set of longer claws 31 engaging a smaller vial closure 73 while the first set of claws 29 remain disengaged. FIG. 8 primarily demonstrates the plastic deformation of the second set of claws 31 while mounting the vial adapter 21 to a vial that is too large for engagement by those larger claws 31. Instead, the shorter claws (first set) 29 engage the vial closure 73.

Figure 9:
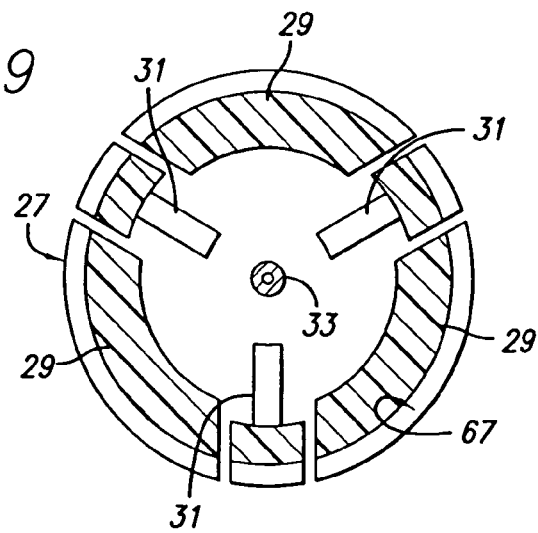
FIG. 9 is an end on view of the vial adapter of FIG. 1 from the sharpened cannula end, illustrating in particular the circular array of first set of claws alternating with the second set of longer claws and also showing the slotted shroud.

FIG. 9 shows a partial view of the vial adapter shown in FIG. 3 along the lines indicated by the "9" numerals. A view of the inner periphery 67 of the shroud 27 is presented showing the alternating placement of the first set of shorter claws 29 with the second set of longer claws 31. In the view of FIG. 9, the second set of claws 31 alternate with the first set of claws 29 about the inner periphery 67 such that each of the claws of the second set of claws is located between two claws of the first set. Because there are three claws in each set and they are spaced equally around the inner periphery 67 in this case, the claws in each set are therefore spaced at 120° from each other in the same set. However, in other embodiments, the claws may be spaced apart at different intervals. The centralized location of the sharpened cannula 33 is also apparent from FIG. 9.

Figure 10:
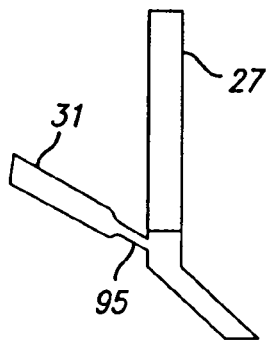
FIG. 10 is an enlarged detailed view of a hinged claw from the second set of claws in FIG. 9.
Figure 11:
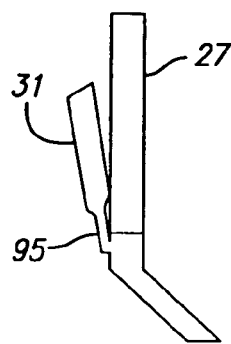
FIG. 11 is an enlarged detailed view of the hinged claw in FIG. 10, specifically illustrating the plastic deformation that takes place at the hinge when the adapter engages a large vial closure.

FIGS. 10 and 11 show an enlarged view of a variation of the second set of claws 31 in which a narrowed segment 95 is included in each of the second set of claws to act as a hinge or plastic deformation point. FIG. 10 specifically shows the claw 31 in its normal, pre-mounting configuration prior to engagement with a vial closure. However, FIG. 11 shows the claw 31 of FIG. 10 in which the narrowed segment 95 has plastically deformed and the claw is permanently in a new "vertical" configuration due to the plastic deformation. Relating FIG. 11 to FIG. 8, plastic deformation of this claw 31 of the second set of claws has occurred during the mounting process of the vial adapter 21 on a larger vial closure, in this embodiment, a closure of approximately 20 mm in diameter.

Figure 12:
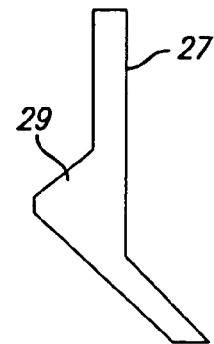
FIG. 12 is an enlarged detailed view of a claw from the first set of claws in FIG. 9.

FIG. 12 presents an enlarged view of a claw 29 from the first set 27 of claws used to engage a vial closure with a larger diameter; e.g., 20 mm.

Figure 13:
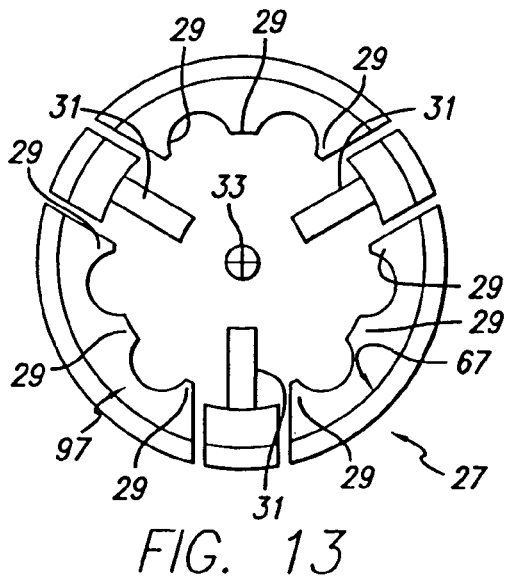
FIG. 13 illustrates an end on view of an alternative embodiment of the vial adapter of FIG. 9, illustrating in particular a different arrangement of the circular array of claws in which there are two shorter claws positioned between each long claw.

FIG. 13 illustrates an alternative embodiment of a circular array of claws 97 wherein the circular array of claws surrounding the sharpened cannula 33 is arranged about the inner periphery 67 of a shroud 27 such that multiples of the first set of shorter claws 29 alternate with one claw 31 from the second set of longer claws 31. In this embodiment, the multiple shorter claws 29 have a serrated appearance and there are three shorter claws 29 between each pair of longer claws 31.

Figure 14:
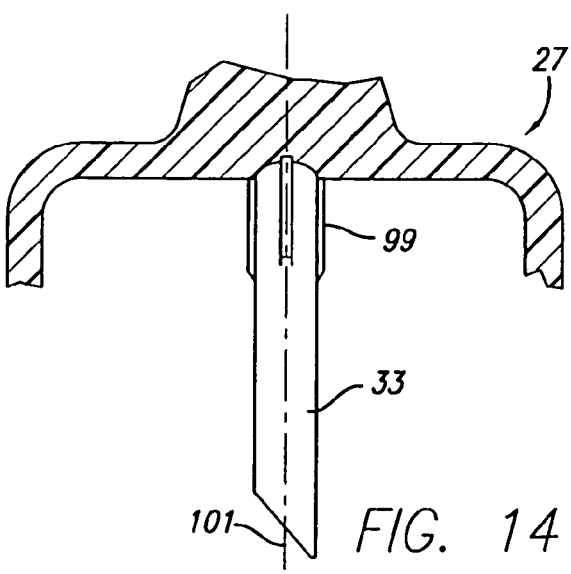
FIG. 14 is an enlarged detailed view of the sharpened cannula in an alternate embodiment, illustrating in particular the protruding ribs extending from the base of the sharpened cannula that resist rotation of the cannula once they have penetrated the stopper of a vial.

Turning now to FIG. 14, the sharpened cannula 33 is shown with a protruding rib 99 located so that when the cannula is engaged with the rubber stopper of a vial closure, the protruding rib will resist rotation of the cannula once the sharpened cannula with the protruding rib have punctured the rubber stopper of the closure. As shown, the protruding rib 99 is elongated and is oriented parallel to a longitudinal axis 101 of the central sharpened cannula 33 In the embodiment show, a plurality of protruding ribs 99 are formed on the sharpened cannula 33 and will resist rotation of the cannula.

Figure 15:
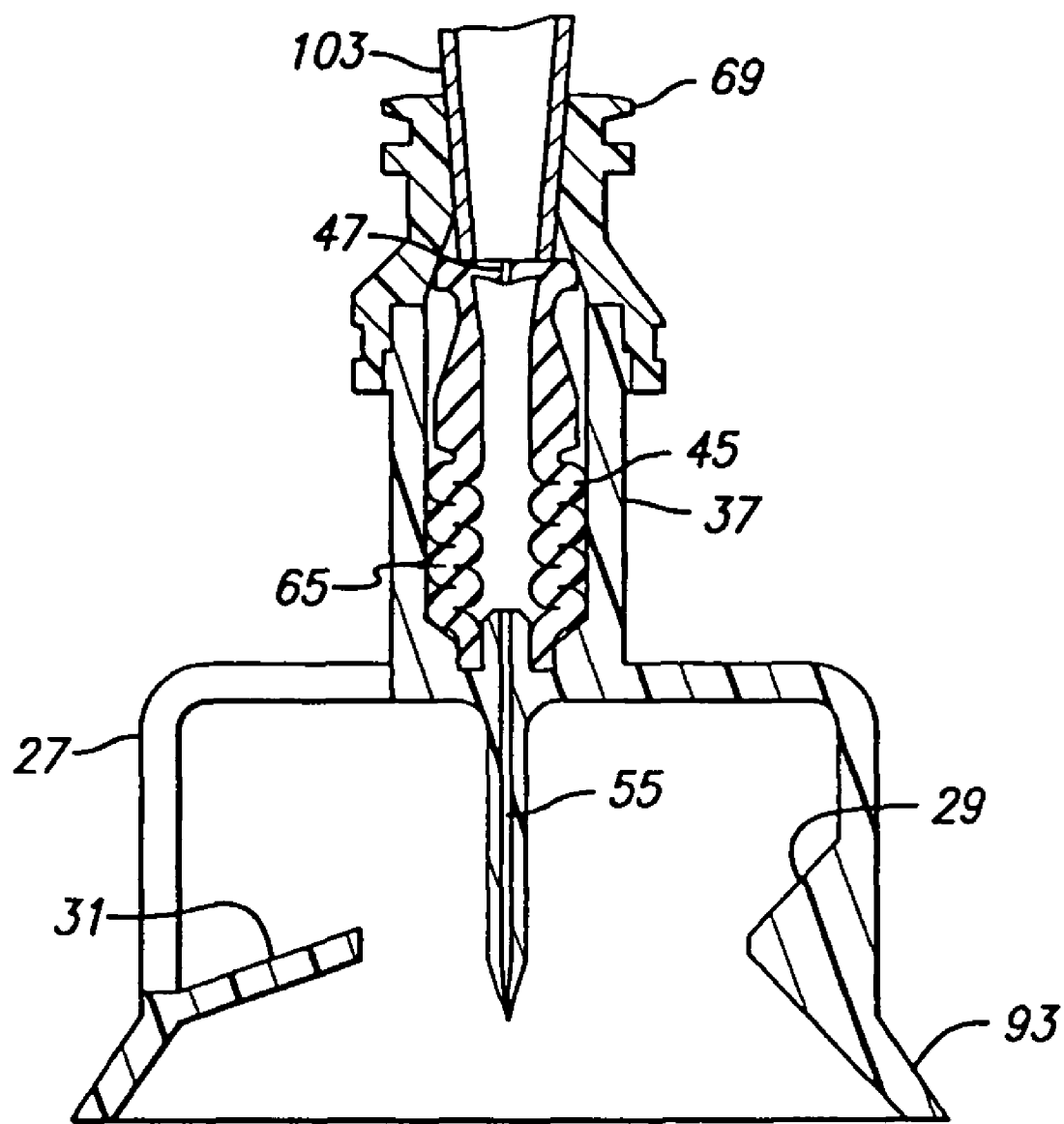
FIG. 15 is a view similar to FIG. 3 except the valve has been accessed by a male Luer connector and in response, the internal resilient piston has returned to its naturally open position to permit fluid flow through the adapter.

FIG. 15 is a view similar to FIG. 3 except the needle-free valve 37 has been accessed by a male Luer connector 103 thereby pressing the piston element 45 further into the valve housing 23 and compressing the spring bellows section 65. In response, the bore 47 of the resilient piston element 45 has returned to its naturally open position to permit fluid flow through the needle-fee valve and through the lumen 55 of the sharp cannula 33 to establish a fluid flow path through the vial adapter.

Figures 16, 17:
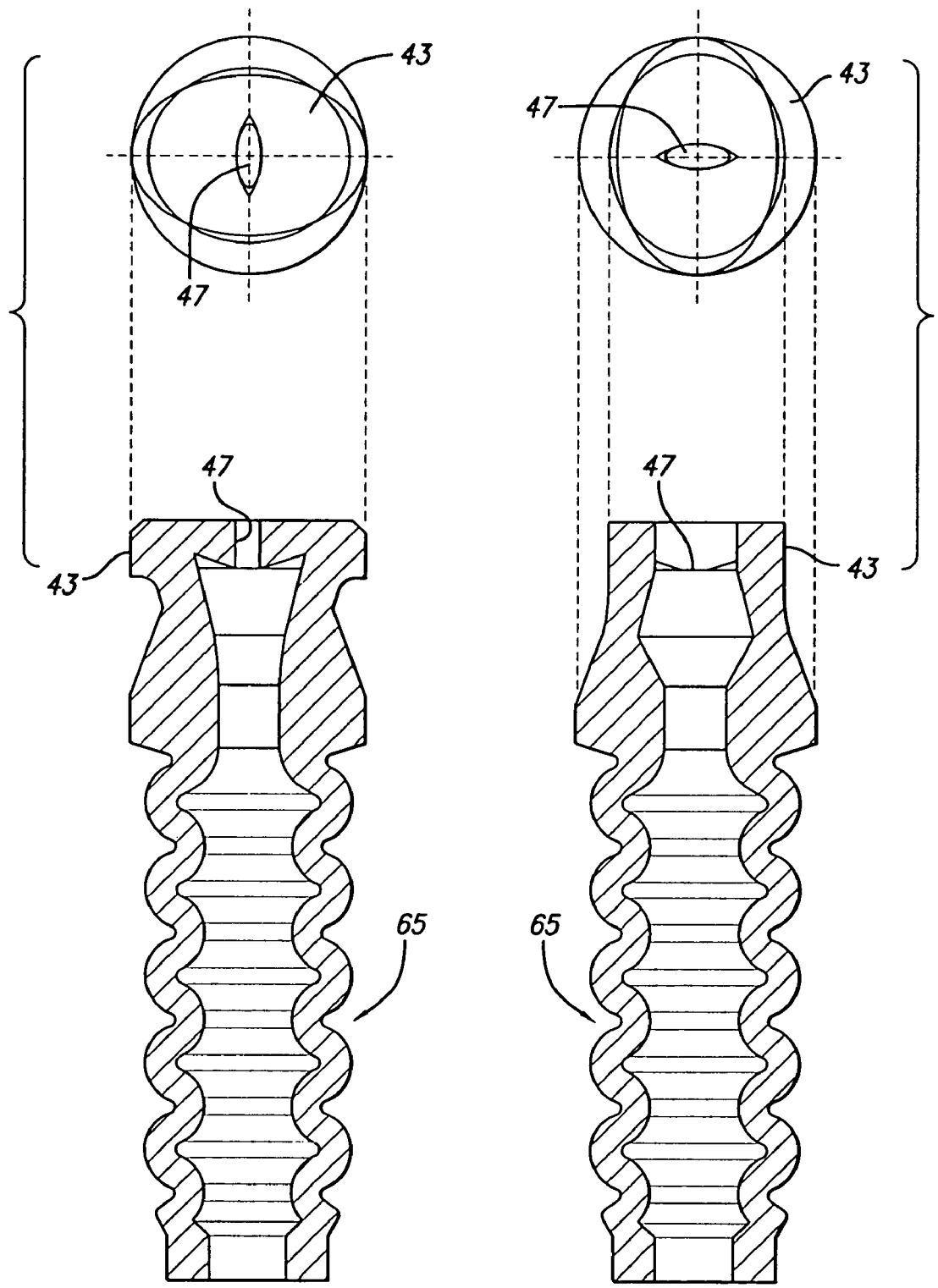
FIGS. 16 and 17 present views of a piston element usable in the needle-free valve of the vial adapter disclosed, showing the elliptical shape of the piston head with the marquise-shaped, naturally open bore.

FIGS. 16 and 17 provide further details of the piston element 45 disclosed and discussed above. The bellows section 65 in these figures has more bellows than the piston element disclosed previously; however, the piston element operates the same as discussed above in regard to FIGS. 3 and 15. The elliptical shape of the piston head 43 with the marquise-shaped, naturally open bore 47 is visible.

Thus it will be appreciated that a versatile vial adapter has been disclosed. The design of the adapter is such that an operator of the adapter is protected from inadvertent punctures by the cannula by a shroud, yet the adapter can easily be used to adapt pierceable septa to use with needle-free devices. Both a sharpened cannula and a needle-free resealable site are included in one adapter thus obviating the need for two separate adapters. The adapter also reduces the need to stock as many different sizes of adapters, as the adapter in accordance to the invention is capable of fitting multiple vial closures.

While particular forms of the invention have been illustrated and described, it will also be apparent to those skilled in the art that various modifications can be made without departing from the spirit and scope of the invention. Accordingly, it is not intended that the invention be limited except by the appended claims.

What is claimed is:

1. A vial adapter for interconnecting with vial closures of different diameters, each closure having a seal, comprising:
an adapter housing having a first end with an inner periphery with a circular array of claws, and having a second end, the housing having a thickness at the inner periphery; and
a sharpened cannula extending from the first end of the adapter housing for penetrating a seal of a vial closure to establish fluid communication between the vial and the first end;
wherein the array of claws comprises:
a first set of claws, each claw of the first set of claws having a first surface extending upwardly and radially inwardly from the inner periphery, and a second surface extending from the first surface upwardly and radially outwardly towards the inner periphery, each of the claws in the first set of claws having a first length so as to cause the inner periphery to expand outwardly when the vial adapter is placed over a closure exceeding a first diameter, the second surface preventing withdrawal of the closure from the vial adapter without expanding the inner periphery outwardly; and
a second set of claws extending radially inwardly from the inner periphery, each of the second set of claws having a second length that is longer than the first length of the first set of claws, each of the second sect of claws adapted such that when the vial adapter is placed over a closure exceeding the first diameter, each of the second set of claws will deflect and plastically deform thereby permitting the second set of claws to accommodate the larger closure.

2. The vial adapter of claim 1 wherein the length of each of the first set of claws is selected to engage a vial closure with at least the first diameter.

3. The vial adapter of claim 1 wherein the length of each of the second set of claws is selected to engage a vial closure with at least a second diameter that is smaller than the first diameter.

4. The vial adapter of claim 1 wherein the second set of claws are thinner than the adapter housing at the inner periphery and plastic deformation of the second set of claws occurs at a location along the length of the thinner second claws.

5. The vial adapter of claim 4 wherein the thickness of the second set of claws is selected so that when plastically deformed, the second set of claws do not apply a force sufficient to decouple the vial adapter from the closure.

6. The vial adapter of claim 1 wherein the second set of claws comprises a narrowed segment at which the plastic deformation takes place.

7. The vial adapter of claim 1 wherein the length of each of the second set of claws is selected such when that the adapter engages the second diameter vial closure, each of the second set of claws deforms elastically to engage the second diameter vial closure.

8. The vial adapter of claim 7 wherein the second set of claws deflect elastically as a result of a force directed axially through the center line of the vial adapter so that the second set of claws will snap under a crimped retaining cap surrounding a rubber stopper placed in the opening of the vial.

9. The vial adapter of claim 1 wherein the second set of claws are located at the inner periphery so that they are alternating with the first set of claws about the inner periphery.

10. The vial adapter of claim 1 wherein the adapter housing further comprises a shroud forming a part of the adapter housing at the first end, the shroud extending from the first end far enough to surround the sharpened portion of the sharpened cannula to protect an operator of the vial adapter from inadvertent puncture by the sharpened cannula.

11. The vial adapter of claim 1 wherein each of the first set of claws has a terminal end and each of the second set of claws has a terminal end and the terminal ends of the first set of claws and the terminal ends of the second set of claws are located in a common plane.

12. The vial adapter of claim 1 further comprising a resealable needle-free vial located in the second end of the adapter housing, wherein the needle-free vial opens to permit fluid flow upon insertion of a blunt cannula and closes to prevent fluid flow upon removal of such blunt cannula.

13. The vial adapter of claim 12 wherein the resealable needed-free vial comprises a vial housing within which is disposed a deformable piston element that provides a fluid flow path through its interior, the piston element having a naturally open bore wherein the bore is closed to prevent fluid flow when the needle-free vial is not accessed and wherein the bore opens to its naturally open shape to permit fluid flow when the vial is accessed.

14. The vial adapter of claim 13 wherein:
the housing of the resealable needle-free vial comprises a connection port, an exit orifice, a first section of a first cross-sectional size disposed adjacent the connection port, and a second section of a second cross-sectional size that is larger than the first section; and
the piston element comprises a deformable piston head in which the bore is formed, the piston head being movable from the first section of the vial housing as the needle-free vial is accessed and movable to the second section of the vial housing when the needle-free vial is not accessed, the first section having a size that deforms the piston head so as occlude the bore, the second section having a size that allows the piston head to assume its natural shape in which the bore is open to provide a fluid flow path between the connection port and the exit orifice.

15. The vial adapter of claim 13 wherein:
the housing of the resealable needle-free vial comprises a connection port and an exit orifice; and
when the needle-free vial is accessed, the interior of the deformable piston element provides the fluid flow path through the needle-free vial between the connection port and the exit orifice.

16. A vial adapter for interconnecting with drug vial closures of different diameters, each closure having a seal, the vial adapter comprising:
an adapter housing having a first end with an inner periphery and a circular array of claws extending radially inward from the periphery, and a second end, the adapter housing having a thickness at the inner periphery;
the first end including a base, a central cannula extending from the base;
a sharpened cannula located at the first end to perforate a vial's rubber stopper and provide fluid communication between the vial and the first end;
wherein the circular array of claws comprises a first set of claws, each claw of the first set of claws having a first surface extending upwardly and radially inwardly from the inner periphery, and a second surface extending from the first surface upwardly and radially outwardly towards the inner periphery, each of the claws in the first set of claws having a first length so as to cause the inner periphery to expand outwardly when the vial adapter is placed over a closure exceeding a first diameter, the second surface preventing withdrawal of the closure from the vial adapter without expanding the inner periphery outwardly;
wherein the circular array of claws comprises a second set of claws, each of which has a second length that is longer than the first length of the first set of claws, each of the second set of claws adapted to deflect and plastically deform when the adapter is placed over a closure exceeding the first diameter, thereby permitting the second set of claws to accommodate the larger closure size; and
a resealable needle-free vial located at the second end of the body that opens to permit fluid flow upon insertion of a blunt cannula and closes to prevent fluid flow upon removal of such blunt cannula.

17. The vial adapter of claim 16 wherein the length of each of the first set of claws is selected to engage a vial closure with at least a second diameter that is smaller than the first diameter.

18. The vial adapter of claim 16 wherein the length of each of the second set of claws is selected to engage a vial closure with at least a second diameter that is smaller than the first diameter.

19. The vial adapter of claim 16 wherein the second set of claws are thinner than the inner periphery and plastic deformation of the second set of claws occurs at a location along the length of the thinner second claws.

20. The vial adapter of claim 16 wherein each of the second set of claws comprises a narrowed segment at which the plastic deformation takes place.

21. The vial adapter of claim 16 wherein the length of each of the second set of claws is selected such that when the adapter engages a vial closure with at least the second diameter, each of the second set of claws deforms elastically to engage the closure.

22. The vial adapter of claim 21 wherein the second set of claws deflect elastically as a result of a force directed axially through the center line of the vial adapter and the claws snap under the vial cap.

23. The vial adapter of claim 16 wherein each of the second set of claws is located at the periphery such that they are alternating with the first set of claws.

24. The vial adapter of claim 16 wherein the adapter housing further comprises a shroud forming a part of the housing at the first end, the shroud extending from the first end far enough to surround the sharpened portion of the sharpened cannula to protect an operator of the vial adapter from inadvertent puncture by the sharpened cannula.

25. The vial adapter of claim 16 wherein the resealable needle-free vial comprises a vial housing within which is disposed a deformable piston element that provides a fluid flow path through its interior, the piston element having a naturally open bore wherein the bore is closed to prevent fluid flow when the needle-free vial is not accessed and wherein the bore opens to its naturally open shape to permit fluid flow when the vial is accessed.

26. The vial adapter of claim 25 wherein:
the housing of the resealable needle-free vial comprises a connection port, an exit orifice, a first section of a first cross-sectional size disposed adjacent the connection port, and a second section of a second cross-sectional size disposed adjacent the connection port, and a second section of a second cross-sectional size that is larger than the first section; and
the piston element comprises a deformable piston head in which the bore is formed, the piston head being movable from the first section of the vial housing as the needle-free vial is accessed and movable to the second section of the vial housing when the needle-free vial is not accessed, the first section having a size that deforms the piston head so as to occlude the bore, the second section having a size that allows the piston head to assume its natural shape in which the bore is open to provide a fluid flow path between the connection port and the exist orifice.

27. The vial adapter of claim 25 wherein:

the housing of the resealable needle-free vial comprises a connection port and an exit orifice; and when the needle-free vial is accessed, the interior of the deformable piston element provides the fluid flow path through the needle-free vial between the connection port and the exit orifice.

28. A vial adapter for interconnecting with drug vial closures of different diameters, each closure having a seal, the vial adapter comprising:

an adapter housing having a first end with an inner periphery and a circular array of claws extending radially inward from the inner periphery, and having a second end, the adapter housing having a thickness at the inner periphery;

wherein the circular array of claws comprises a first set of claws each of which has a first length and a second set of claws each of which has a second length that is longer than the first length;

wherein each claw of the first set of claws has a first surface extending upwardly and radially inwardly from the inner periphery, and a second surface extending from the first surface upwardly and radially outwardly towards the inner periphery, each of the claws in the first set of claws having the first length so as to cause the inner periphery to expand outwardly when the vial adapter is placed over a closure exceeding a first diameter, the second surface preventing withdrawal of the closure from the vial adapter without expanding the inner periphery outwardly;

wherein each claw of the second set of claws is thinner than the inner periphery and plastic deformation of the second set of claws occurs at a location at which the second set of claws are joined to the inner periphery such that when the adapter is placed over a closure exceeding the first diameter, each of the second set of claws deflects upon contact with the closure and plastically deforms permitting the claws to deflect sufficiently to accommodate the larger closure; and a needle-free vial comprising a vial housing within which is disposed a deformable piston element that provides a fluid flow path through its interior, the piston element having a naturally open bore wherein the bore is closed to prevent fluid flow when the needle-free vial is not accessed and wherein the bore opens to its naturally open shape to permit fluid flow when the vial is accessed.

\* \* \* \* \*